United States Patent [19]
Bialousz et al.

[11] 3,965,035
[45] June 22, 1976

[54] ENZYME CARRIER REGENERATION

[75] Inventors: Lorraine R. Bialousz, Elmira; Ethel R. Herritt; Donald J. Lartigue, both of Corning; Wayne H. Pitcher, Jr., Painted Post, all of N.Y.

[73] Assignee: Corning Glass Works, Corning, N.Y.

[22] Filed: Sept. 18, 1974

[21] Appl. No.: 507,199

[52] U.S. Cl. .............................. 252/412; 195/31 F; 195/63; 195/68; 195/DIG. 11; 251/413
[51] Int. Cl.² ................. B01J 21/20; G11B 19/08; G07F 11/00
[58] Field of Search .................. 252/413, 414, 412; 195/31 F, 63, 68, DIG. 11

[56] References Cited
UNITED STATES PATENTS

| | | | |
|---|---|---|---|
| 3,676,364 | 7/1972 | Coates | 252/413 |
| 3,839,175 | 10/1974 | Keyes | 195/63 |
| 3,847,740 | 11/1974 | Heady et al. | 195/31 F |
| 3,850,751 | 11/1974 | Messing | 195/63 |
| 3,868,304 | 2/1975 | Messing | 195/31 F |

Primary Examiner—Helen M. McCarthy
Assistant Examiner—P. E. Konopka
Attorney, Agent, or Firm—James A. Giblin; Clinton S. Janes, Jr.; Clarence R. Patty, Jr.

[57] ABSTRACT

Highly porous $MgO$-$Al_2O_3$ support materials useful for the immobilization of glucose isomerase can be regenerated for reuse by pyrolysis under conditions sufficient to remove substantially all carbonaceous matter, followed by treatment with a neutralized citrate solution.

9 Claims, No Drawings

ENZYME CARRIER REGENERATION

RELATED APPLICATIONS

Patent application Ser. No. 332,807 entitled "Enzymes Immobilized on Porous Inorganic Support Materials", now U.S. Pat. No. 3,850,751 and patent application Ser. No. 332,739 entitled "Method of Making Fructose with Immobilized Glucose Isomerase", now U.S. Pat. No. 3,868,304, both filed on Feb. 16, 1973 in the name of R. A. Messing and Ser. No. 507,209, filed of even date herewith in the names of D. L. Eaton et al. entitled "Immobilized Glucose Isomerase", all three applications being assigned to the present assignee.

BACKGROUND OF THE INVENTION

1. Field

This disclosure is concerned generally with porous inorganic support materials useful for the immobilization of enzymes and specifically with methods of regenerating certain such carriers which have been found useful for the immobilization of glucose isomerase.

2. Prior Art

In patent applications Ser. No. 332,807 and Ser. No. 332,739, cited above, there are disclosed methods of immobilizing glucose isomerase within the pores of high surface area, highly porous alumina particles to provide a very efficient and reuseable immobilized glucose isomerase system useful for the isomerization of glucose to fructose. As described in those patent applications, it was found that the porous alumina carrier, preferably in particulate form (e.g. within 4-200 mesh), should have an average pore diameter at least as large as the enzyme, but less than about 1000A, preferably less than 500A or between about 100A and 500A. In patent application Ser. No. 507,209, cited above, and filed of even date with this application, an improvement over the alumina carrier is disclosed. The improved glucose isomerase carriers have incorporated thereinto varying amounts of magnesia, the preferred carriers consisting of both alumina and magnesia with the magnesia preferably constituting about 0.84 to 12.0% by weight. Such carriers are referred to herein as $MgO-Al_2O_3$ carriers to distinguish them from the $Al_2O_3$ carriers.

In using either porous $Al_2O_3$ or porous $MgO-Al_2O_3$ carriers for the adsorption and, hence, immobilization of glucose isomerase, it has been found that the resulting composites demonstrate a high degree of stability and relatively long enzymatic half-lives. These qualities make the composites commercially attractive since such characteristics are desirable for any large scale conversion of glucose-containing solutions to fructose-containing solutions. The desirability of being able to continuously and economically convert glucose to fructose is well recognized, especially via enzymatic isomerization methods.

Even though the above-described porous $Al_2O_3$ and porous $MgO-Al_2O_3$ carriers can be used to prepare immobilized glucose isomerase compositions having relatively long half-lives, the use, especially the continuous use, of such composites is economically time-limited. Regardless of the length of enzymatic half-life of the composites, it can be appreciated that the total enzymatic activity tends to decline with time. Thus, at a given point in time, it becomes uneconomical to continue using the composites because of reduced activity. Accordingly, at that time it becomes more economical to simply replace the spent composite with fresh composite.

Although the above-described porous carriers are relatively inexpensive and can be discarded after use without detracting significantly from the overall favorable economics of using such carriers for glucose isomerase, it would be highly desirable if the carriers could be regenerated for reuse. Carrier reuse would not only permit yet further economies, but also avoid problems associated with discharge of the spent composites. It is known that various pyrolysis treatments can be used to burn off organic constituents on inorganic materials. We have found, however, that a relatively simple pyrolysis step per se is not sufficient to prepare the porous carrier for immediate and economical reuse because the pyrolyzed carriers still have associated therewith various contaminants (e.g., various metal ions from the substrate) which tend to minimize subsequent enzyme loading and/or half-life. Quite surprisingly, we have found that the carriers can be readily regenerated for economical reuse by a controlled pyrolytic step followed by treatment with a solution which appears to remove undesirable metal ions associated with the carriers after pyrolysis. Our two-step method of regenerating the carriers is described in detail below and this disclosure is directed specifically toward methods of regenerating the $MgO-Al_2O_3$ carriers disclosed in patent application Ser. No. 507,209, filed herewith in the names of D. L. Eaton et al.

SUMMARY OF THE INVENTION

Our method of regenerating the highly porous $MgO-Al_2O_3$ carriers useful for the immobilization of glucose isomerase comprises the steps of pyrolyzing the carriers under conditions sufficient to remove substantially all carbonaceous matter and then treating the carriers with a neutralized citrate solution. Our preferred carrier materials consist of highly porous particles consisting of $MgO-Al_2O_3$ having incorporated therein between about 0.84% and 12.0% by weight MgO, the particles having an average pore diameter between about 100A and 1000A, very preferably between about 150A and 250A and an average particle size between about 4 and 200 mesh, preferably 30 to 45 mesh, U.S. Standard Sieve. The preferred regeneration steps involve subjecting such particles to a temperature of between 500°C. and 900°C. in the presence of oxygen for a period of time sufficient to remove substantially all carbonaceous matter from the carrier. Thereafter, the particles are permitted to cool and are then exposed to a neutralized aqueous solution of citrate ions for a period of time sufficient to remove contaminants such as metal ions which would otherwise minimize the economical reuse of the carrier. Preferably the citrate solution consists of about a 0.1 molar citrate solution, maintained at a pH between about 6.0 and 10, very preferably a sodium citrate solution at a pH of about 7.0, and the pyrolyzed carrier is incubated with the citrate solution for at least about 15 minutes, preferably at room temperature.

SPECIFIC EMBODIMENT

As noted above, the present invention is directed specifically toward methods of regenerating the porous $MgO-Al_2O_3$ carrier materials useful as carriers for glucose isomerase which carriers are described in detail in the cited and copending patent application filed in the name of D. L. Eaton et al. As disclosed, those carriers comprise porous $MgO-Al_2O_3$ materials consisting of alumina and about 0.84% to 12.0% magnesia (by wt.). For reasons given in the copending applications, it has been found that the average particle size of the porous carriers should be between about 4 and 200 mesh, preferably between about 30 and 45 mesh and the average pore diameter of the individual particles should be between about 100A and about 1000A, preferably between about 100A and 500A. Specifically, it has been found that an ideal $MgO-Al_2O_3$ carrier for the immobilization (by adsorption) of glucose isomerase has an average pore diameter between about 150A and 250A. Since the $MgO-Al_2O_3$ is an especially preferred carrier for the preparation of an immobilized glucose isomerase composite, our methods are directed specifically toward regenerating that carrier, although it is thought the regeneration would also work well on pure $Al_2O_3$ carriers.

As pointed out above, our regenerative method consists of two essential steps: pyrolysis and treatment with the citrate solution. The necessity of both steps can be appreciated by noting the requirements for a fresh reuseable carrier vis-a-vis the condition of a spent composite. As used herein, the expression "spent" composite refers to the immobilized glucose isomerase composite which, after some use, has become uneconomical to use further. Several factors may determine the point in time at which the composite is uneconomical to use. For example, the enzymatic half life or amount of active glucose isomerase on the carrier may have dropped to a relatively low level. The composite may have become contaminated with various microbial growths which preclude further economical use. Further, the composite may be contaminated with an undesirable excess of various metal ions which become associated with the composite after prolonged contact with the glucose-containing solution, to which various buffers containing such ions are often added. As shown in Ser. No. 332,739, a preferred reactor system for the continuous conversion (isomerization) of glucose to fructose consists of a plugged flow-through column through which a buffered glucose solution is continuously passed. The glucose solution is commonly buffered to a pH range in which optimum isomerization can occur and the temperature of the glucose solution and/or the column is commonly elevated, also to assure optimum isomerization without significant enzyme deactivation.

In using such a continuous processing system, various ions from the buffers tend to associate with the composite, the amounts of which tend to increase with time. Although a relatively simple pyrolysis step is sufficient to remove the spent enzyme and other carbonaceous materials (e.g., sugars, microbes, etc.) in the carrier, pyrolysis will not remove the accumulated metal ions in the composite. Rather, the heating step will tend to leave residual metal oxide contaminants in and on the carrier surface. Since an accumulation of such metals minimizes the economical reuse of the carrier, it is highly desirable to have them removed to bring the porous carriers back to a near pristine condition prior to the re-immobilization by adsorption of the glucose isomerase.

The essence of our discovery is that by treating the post-pyrolyzed carrier with a food-grade chelating agent (citrate ions), the accumulated metal ions can be removed and the carrier surface brought back very nearly to its original state. As used herein, the term "neutralized" refers to a citrate solution having a pH within the range of 6.0 to 10.0.

Since the citrate treatment may be accomplished by continuously passing the citrate solution through a plugged flow-through column containing the pyrolyzed carrier, prior to re-adsorption of fresh enzyme, the treatment minimizes the need for further processing equipment.

In the examples below, we compare the enzymatic activities of composites having new (pristine) carriers with composites having pyrolyzed carriers and pyrolyzed and citrate-treated carriers. Further, we show that by using our two-step regeneration method, the carriers of the spent composite can be subject to at least six regeneration treatments without significant loss in utility as a glucose isomerase carrier.

In all examples below, we used a $MgO-Al_2O_3$ porous carrier consisting by weight of about 2.0 to 2.4% MgO. The carrier was in particulate form having an average particle size between about 30 and 45 mesh, U.S. Standard Sieve. The individual particles had an average pore diameter of about 200A, with minimum pore diameter of about 150A and a maximum pore diameter of about 250A. The carrier had a surface area of about 100 $M^2/g$. Such carriers can be made by mixing a slurry of $Al_2O_3$ particles (about 300 ±200A average particle size) with an aqueous solution of $MgCl_2$, drying the slurry to remove most water and then firing the dried material at a temperature below the sintering point. The resulting dried porous bodies can then be sorted according to mesh size by conventional methods. Specific directions for forming the $MgO-Al_2O_3$ porous bodies are given in the cited copending application filed in the name of D. L. Eaton et al.

The glucose isomerase solution used to prepare the immobilized enzyme composites was an aqueous solution having a glucose isomerase activity of about 2,700 International Glucose Isomerase Units, IGIU, per ml. One IGIU designates an enzymatic activity need to produce $1\mu$ mole of fructose per min. at 60°C., pH 6.85 from a solution of 2M glucose solution. The enzyme was derived from a Streptomyces sp. organism.

The composites were prepared by reacting 10 ml. of the enzyme solution with 10 g. of the porous carrier as follows: The carriers are initially washed with distilled water in a fluidizing column. The carrier is then placed in a flask to which 10 ml/gram carrier of 0.05M magnesium acetate is added and the flask is placed in a shaker bath for 1 hour. The solution is then decanted and the enzyme solution is added and this mixture is allowed to react in the shaker bath for 24 hours to facilitate enzyme adsorption. The product is then rinsed with distilled water and the immobilized enzyme composite can be stored in water or as a wet cake until used.

Enzyme Activity Determinations

The performance of each enzyme composite was observed by placing 10 gram samples of the composite in a 1.5 cm diameter column through which a 50% glucose solution (Cerelose cation exchanged) was continuously passed. The feed solution was maintained at 60°C., and contained 0.005M $MgCl_2$ brought to pH 8.4 with sodium hydroxide. Activity was calculated as $$E = 27.9 \; \frac{F}{W} \; \ln \; \frac{1}{1 - X/Xe}$$

where $E$ = activity units, $F$ = flow rate in ml/hr, $W$ = immobilized enzyme composite weight in grams (dry basis), $X$ = % fructose produced, and $X_e$ = % fructose at equilibrium (51.2%).

In preparing the composites of the examples, approximately 10 gram (wet weight) quantities of each composite were prepared by the above methods. Nine separate composites were prepared with new carrier (unregenerated). Each new carrier was then "spent" by placing it in a plug flow through column through which the glucose solution was flowed continuously under assay conditions for at least 30 days.

Then, the indicated number of samples were regenerated by pyrolysis, and pyrolysis followed by citrate treatment, as indicated. The pyrolysis step involved heating the carriers to a temperature of 500 to 600°C. for 1 hour in the presence of an oxygen source. The citrate solution treatment involved pumping 0.1 m citric acid solution neutralized to pH 7.0 (with NaOH) through a packed bed (plugged flow-through column) of the pyrolyzed carrier for about 1 hour, the amount of the citrate solution being about 3 ml. per gram of pyrolyzed carrier treated.

EXAMPLES I–II

Regeneration of MgO-Al₂O₃ Porous Carriers

Table I shows the initial activities of adsorbed glucose isomerase preparations in laboratory column operation using 50% glucose (Cerelose) feed containing 0.005 M $MgCl_2$ at pH 8.4 and 60°C. The benefits of citrate treatment are evident.

TABLE I

| Carrier Description (Examples) | Number of Samples | Average Initial Activity (Units/g) |
|---|---|---|
| New carrier | 6 | 854 |
| Pyrolysis and citrate (1) | 4 | 895 |
| Pyrolysis (no citrate) | 1 | 781 |
| New carrier | 3 | 688 |
| Pyrolysis and citrate (2) | 2 | 736 |
| Pyrolysis (no citrate) | 1 | 616 |

EXAMPLES III–VIII

Successive Regenerations of MgO-Al₂O₃ Carriers

The feasibility of regenerating the same carrier a number of times is shown in Table II. Enzyme activity half-lives were measured during composite use for at least 30 days for each successive operating cycle.

TABLE II

| Description (Examples) | AIM Initial Activity (IGIU/g) | Half-Life (days) 95% | | |
|---|---|---|---|---|
| | | Mean | LCL | UCL |
| NEW CARRIER | 860 | 29.5 | 28.4 | 30.7 |
| 1st regeneration (3) | 874 | 32.3 | 30.4 | 34.4 |
| 2nd regeneration (4) | 933 | 24.3 | 22.8 | 26.0 |
| 3rd regeneration (5) | 872 | 26.9 | 25.2 | 28.8 |
| 4th regeneration (6) | 1010 | 28.0 | 26.0 | 30.2 |
| 5th regeneration (7) | 1008 | 42.0 | 35.6 | 51.2 |
| 6th regeneration (8) | 993 | 32.0 | 29.5 | 34.9 |

We claim:
1. A method of regenerating a porous inorganic support material used for the adsorption of glucose isomerase and comprising porous particles of a MgO-Al₂O₃ composition wherein the amount of MgO is within the range of about 0.84 to 12.0% by weight, the particles have an average particle size within the range of about 4 to 200 mesh, U.S. Standard Sieve, and an average pore diameter within the range of about 100A to 1000A, the method comprising the steps of pyrolyzing the material at a temperature within the range of about 500°C. to 900°C. under conditions sufficient to remove essentially all carbonaceous matter and then reacting the material with an aqueous solution of citrate ions, the solution having a pH between about 6.0 and 10.0.

2. The method of claim 1 wherein the citrate solution is about a 0.1 molar sodium citrate solution, having a pH of about 7.0.

3. The method of claim 2 wherein the amount of citrate solution used is about 3 ml. for each gram of carrier.

4. The method of claim 1 wherein the treatment with the citrate solution occurs in a plugged flow-through column containing the support material and through which the citrate solution is continuously passed.

5. The method of claim 1 wherein the pyrolysis is at a temperature of between about 600°C. and 900°C. for at least about 1 hour.

6. The method of claim 5 wherein the reaction with the citrate solution occurs within a plugged flow-through column containing the support material.

7. The method of claim 1 wherein the pyrolysis is at a temperature of about 500–600°C. for about 1 hour and the citrate solution consists of a 0.1 molar sodium citrate solution neutralized to a pH of about 7.0.

8. The method of claim 7 wherein the treatment with the citrate solution is accomplished by continuously passing the solution through a plugged flow-through column containing the support material.

9. The method of claim 8 wherein the amount of citrate solution is about 3 ml. for each gram of support material in the column.

\* \* \* \* \*

UNITED STATES PATENT OFFICE
CERTIFICATE OF CORRECTION

PATENT NO. : 3,965,035

DATED : June 22, 1976

INVENTOR(S) : Lorraine R. Bialousz, Ethel R. Herritt, Donald J. Lartigue and Wayne H. Pitcher, Jr.

It is certified that error appears in the above-identified patent and that said Letters Patent are hereby corrected as shown below:

Column 4, line 67, "$E = 27.9 \frac{F}{W} \ln \frac{1}{1-X/Xe}$" should be -- $E = 27.9 \left(\frac{F}{W}\right) \ln \left(\frac{1}{1-X/Xe}\right)$ --.

Signed and Sealed this

Thirtieth Day of November 1976

[SEAL]

Attest:

RUTH C. MASON
*Attesting Officer*

C. MARSHALL DANN
*Commissioner of Patents and Trademarks*